US00PP19930P2

(12) United States Plant Patent
Hansen

(10) Patent No.: US PP19,930 P2
(45) Date of Patent: Apr. 21, 2009

(54) ***ASTER* PLANT NAMED 'VICTORIA MATHILDE'**

(50) Latin Name: *Aster novi-belgii*
Varietal Denomination: Victoria Mathilde

(75) Inventor: Erwin Hansen, Hornslet (DK)

(73) Assignee: AsterKlubben, Hornslet (DK)

( * ) Notice: Subject to any disclaimer, the term of this patent is extended or adjusted under 35 U.S.C. 154(b) by 0 days.

(21) Appl. No.: 11/787,687

(22) Filed: Apr. 16, 2007

(51) Int. Cl.
*A01H 5/00* (2006.01)

(52) U.S. Cl. ..... Plt./355
(58) Field of Classification Search ..... Plt./355
See application file for complete search history.

*Primary Examiner*—Annette H Para
*Assistant Examiner*—Georgia Helmer
(74) *Attorney, Agent, or Firm*—C. A. Whealy

(57) ABSTRACT

A new and distinct cultivar of *Aster* plant named 'Victoria Mathilde', characterized by its uniform, upright and mounded plant habit; freely branching growth habit; uniform and freely flowering habit; and decorative-type inflorescences with red purple-colored ray florets.

1 Drawing Sheet

Botanical designation: *Aster novi-belgii*.
Cultivar denomination: 'Victoria Mathilde'.

BACKGROUND OF THE INVENTION

The present invention relates to a new and distinct cultivar of *Aster* plant, botanically known as *Aster novi-belgii* and hereinafter referred to by the name 'Victoria Mathilde'.

The objective of the breeding program is to create new container-type *Aster* cultivars with uniform and rounded plant growth habit, good vigor and strong branching habit and strong floret colors.

The new *Aster* originated from an open-pollination in September, 2003 in Aarslev, Denmark of the *Aster novi-belgii* cultivar Helen Ballard, not patented, as the female, or seed, parent with an unknown *Aster novi-belgii* seedling selection, as the male, or pollen, parent. The new *Aster* was discovered and selected by the Inventor as a single flowering plant within the progeny of the stated open-pollination in a controlled environment in Aarslev, Denmark on Apr. 12, 2004.

Asexual reproduction of the new *Aster* by vegetative tip cuttings was first conducted in Aarslev, Denmark in May, 2004. Asexual reproduction by cuttings has shown that the unique features of this new *Aster* are stable and reproduced true to type in successive generations.

SUMMARY OF THE INVENTION

Plants of the cultivar Victoria Mathilde have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Victoria Mathilde'. These characteristics in combination distinguish 'Victoria Mathilde' as a new and distinct potted *Aster* cultivar:

1. Uniform, upright and mounded plant habit.
2. Freely branching growth habit.

3. Uniform and freely flowering habit.
4. Decorative-type inflorescences with red purple-colored ray florets.

Plants of the new *Aster* differ from plants of the female parent, the cultivar Helen Ballard, in the following characteristics:

1. Plants of the new *Aster* are more vigorous than plants of the cultivar Helen Ballard.
2. Plants of the new *Aster* flower have decorative-type inflorescences whereas plants of the cultivar Helen Ballard have daisy-type inflorescences.
3. Ray florets of plants of the new *Aster* do not fade as quickly as ray florets of plants of the cultivar Helen Ballard.

Plants of the new *Aster* can be compared to plants of the *Aster* cultivar Victoria Red Gaby, not patented. In side-by-side comparisons conducted in Aarslev, Denmark, plants of the new *Aster* differed from plants of the cultivar Victoria Red Gaby in the following characteristics:

1. Plants of the new *Aster* were more vigorous than plants of the cultivar Victoria Red Gaby.
2. Plants of the new *Aster* had smaller inflorescences than plants of the cultivar Victoria Red Gaby.
3. Inflorescences of plants of the new *Aster* had more ray florets than inflorescences of plants of the cultivar Victoria Red Gaby.
4. Ray florets of plants of the new *Aster* did not fade as quickly as ray florets of plants of the cultivar Victoria Red Gaby.
5. Plants of the new *Aster* had longer lasting postproduction longevity than plants of the cultivar Victoria Red Gaby.

BRIEF DESCRIPTION OF THE PHOTOGRAPHS

The accompanying photographs illustrate the overall appearance of the new *Aster*. These photographs show the colors as true as it is reasonably possible to obtain in colored reproductions of this type. Colors in the photographs may differ slightly from the color values cited in the detailed botanical description which accurately describe the colors of the new *Aster*.

The photograph at the top of the sheet comprises a side perspective view of a typical flowering plant of 'Victoria Mathilde' grown in a container.

The photograph at the bottom of the sheet is a close-up view of a typical inflorescence of 'Victoria Mathilde'.

DETAILED BOTANICAL DESCRIPTION

The aforementioned photographs and following observations and measurements describe plants grown during the summer in Hornslet, Denmark in a glass-covered greenhouse and under conditions and practices which approximate those generally used in commercial container *Aster* production. During the production of the plants, day and night temperatures averaged 20° C. Rooted cuttings were planted in 10.5-containers. Plants used in the photographs and for the description were about three months old. In the following description, color references are made to The Royal Horticultural Society Colour Chart, 1995 Edition, except where general terms of ordinary dictionary significance are used.

Botanical classification: *Aster novi-belgii* cultivar Victoria Mathilde.

Parentage:

*Female, or seed, parent.*—*Aster novi-belgii* cultivar Helen Ballard, not patented.

*Male, or pollen, parent.*—Unknown *Aster novi-belgii* seedling selection, not patented.

Propagation:

*Type.*—Terminal vegetative cuttings.

*Time to initiate roots.*—About eight to ten days at temperatures of about 20° C.

*Time to produce a rooted young plant.*—About 12 to 14 days at temperatures of about 20° C.

*Root description.*—Fine; white in color.

*Rooting habit.*—Freely branching.

Plant description:

*Appearance.*—Herbaceous daisy-type potted *Aster*. Upright with lateral branches somewhat outwardly spreading; inverted triangle with mounded crown. Strong and freely branching growth habit with about ten primary lateral branches each with numerous secondary branches. Vigorous growth habit.

*Plant height.*—About 14 cm.

*Plant width.*—About 22 cm.

*Lateral branches.*—Length: About 10 cm. Diameter: About 2 mm to 4 mm. Internode length: About 1 cm to 3 cm. Strength: Moderately strong. Texture: Slightly pubescent. Color: Close to 131B.

Foliage description:

*Arrangement.*—Alternate, simple; sessile.

*Length.*—About 3 cm to 3.5 cm.

*Width.*—About 8 mm to 11 mm.

*Shape.*—Lanceolate.

*Apex.*—Acute.

*Base.*—Cuneate.

*Margin.*—Entire; ciliate.

*Texture, upper and lower surfaces.*—Smooth, glabrous; leathery.

*Color.*—Developing foliage, upper surface: Close to 146B. Developing foliage, lower surface: Close to 137B. Fully expanded foliage, upper surface: Close to 147B; venation, 147B. Fully expanded foliage, lower surface: Close to 137B; venation, 137A.

Inflorescence description:

*Appearance.*—Daisy-type inflorescence form with narrowly obovate-shaped ray florets. Inflorescences borne on terminals above and beyond the foliage. Disk and ray florets arranged acropetally on a capitulum. Inflorescence not fragrant.

*Flowering response.*—Under natural conditions, plants flower during the summer in Denmark. Inflorescences persistent. Inflorescences last about four weeks on the plant.

*Quantity of inflorescences.*—Freely flowering, about 22 inflorescences develop per lateral branch.

*Inflorescence bud.*—Height: About 4 mm to 6 mm. Diameter: About 3 mm to 5 mm. Shape: Ovoid. Color: Close to 137A.

*Inflorescence size.*—Diameter: About 2.5 cm to 3 cm. Depth (height): About 1.1 cm to 1.4 cm. Diameter of disc: Disc florets have not been observed. Receptacle height: About 5 mm to 10 mm. Receptacle diameter: About 1.2 cm to 1.4 cm. Receptacle color: Close to 137A.

*Ray florets.*—Length: About 1 cm to 1.5 cm. Width: About 1 mm to 3 mm. Shape: Narrowly obovate. Apex: Rounded. Base: Attenuate. Margin: Entire. Texture, upper and lower surfaces: Smooth, glabrous, satiny. Orientation: Initially upright, then about 90° from vertical or perpendicular to peduncle. Number of ray florets per inflorescence: About 150 arranged in about six to ten whorls. Color: When opening, upper surface: Close to 74B. When opening, lower surface: Close to 81B. Fully opened, upper surface: Close to 74B; color becoming closer to 78B with development. Fully opened, lower surface: Close to 81C; color becoming closer to 80C with development.

*Phyllaries.*—Number of phyllaries per inflorescence: About 35 to 45 arranged in about four to six whorls. Length: About 8 mm to 12 mm. Width: About 4 mm to 6 mm. Shape: Elliptic. Apex: Acute. Base: Rounded. Texture, upper and lower surfaces: Smooth, glabrous; leathery. Color, upper surface: Close to 132A. Color, lower surface: Close to 132B.

*Peduncles.*—Length: About 1.2 cm to 1.5 cm. Diameter: About 1 mm to 3 mm. Angle: Upright to about 45° from vertical. Strength: Strong, flexible. Texture: Smooth, glabrous; longitudinally ridged. Color: Close to 136B.

*Reproductive organs.*—Androecium: Filament length: About 1 mm. Filament color: Close to 1C. Anther shape: Obovate. Anther length: Less than 1 mm. Anther color: Close to 4D. Pollen amount: Moderate. Pollen color: Close to 12A. Gynoecium: Pistil length: About 2 mm. Stigma shape: Bi-parted. Stigma color: Close to 3D. Style length: About 1 mm. Style color: Close to 3D. Ovary color: Close to 3D.

*Seed/fruit.*—Seed and fruit production has not been observed.

Disease/pest resistance: Resistance to pathogens and pests common to *Asters* has not been observed on plants grown under commercial conditions.

Garden performance: Plants of the new *Aster* have been observed to be rain and wind tolerant and to tolerate temperatures from 5° C. to about 35° C.

It is claimed:

1. A new and distinct *Aster* plant named 'Victoria Mathilde' as illustrated and described.

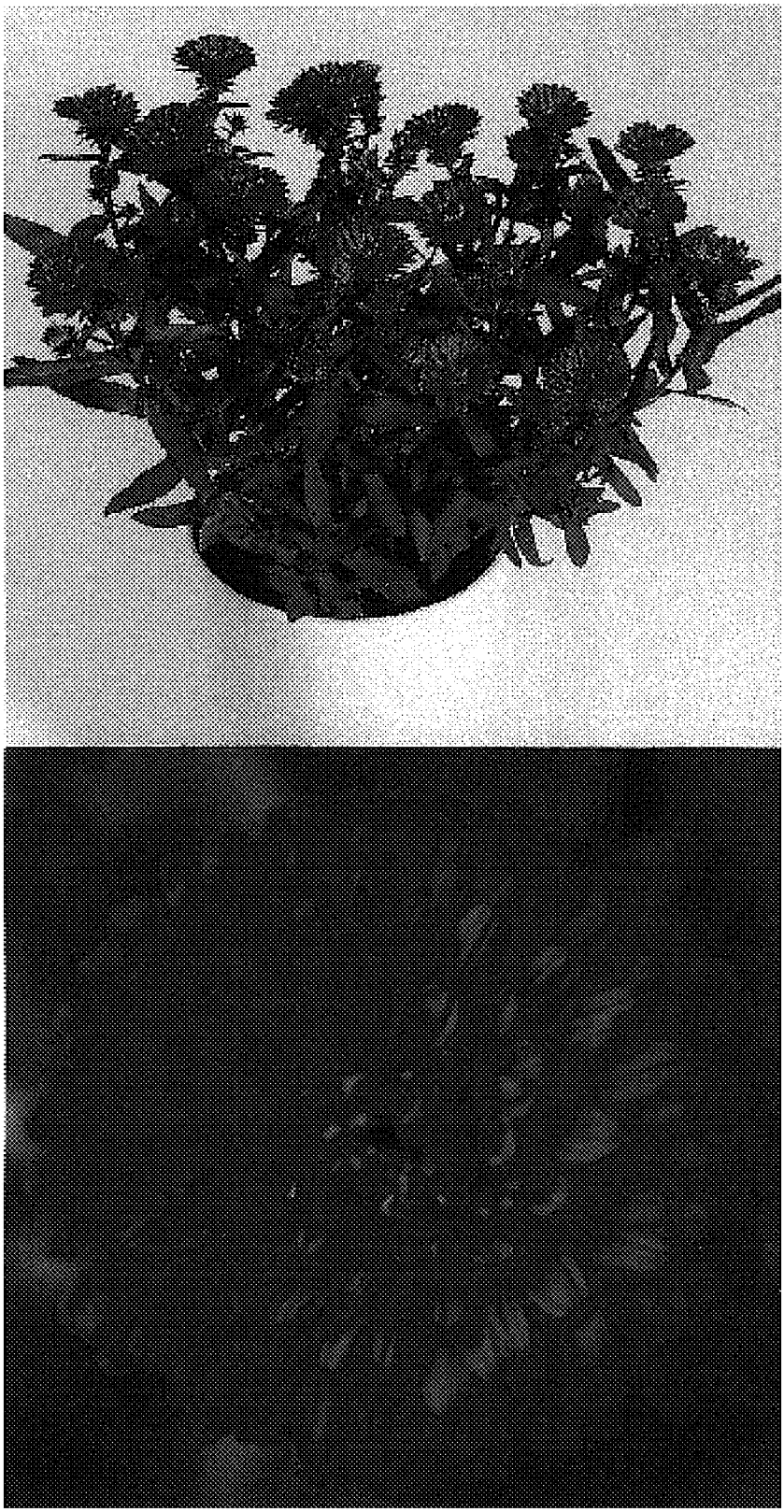

* * * * *